United States Patent [19]

Wang

[11] Patent Number: 5,425,723

[45] Date of Patent: Jun. 20, 1995

[54] INFUSION CATHETER WITH UNIFORM DISTRIBUTION OF FLUIDS

[75] Inventor: James C. Wang, Norton, Mass.

[73] Assignee: Boston Scientific Corporation, Watertown, Mass.

[21] Appl. No.: 179,507

[22] Filed: Dec. 30, 1993

[51] Int. Cl.⁶ .............................................. A61M 25/00
[52] U.S. Cl. ................................... 604/280; 604/264; 138/114
[58] Field of Search ................ 604/29, 39, 43, 48, 604/246, 247, 258, 264, 275, 280; 137/844, 845, 849; 138/111, 114, 118

[56] References Cited

U.S. PATENT DOCUMENTS

| | | | |
|---|---|---|---|
| 3,384,089 | 5/1968 | Shriner | 604/247 |
| 3,426,544 | 2/1969 | Curtis . | |
| 3,601,320 | 8/1971 | Du Plessis | 138/114 X |
| 3,698,195 | 10/1972 | Chapin | 61/12 |
| 4,318,402 | 3/1982 | Vaillancourt | 604/280 |
| 4,927,418 | 5/1990 | Dake et al. | 604/264 |
| 4,961,731 | 10/1990 | Bodicky et al. | 604/264 |
| 4,968,306 | 11/1990 | Huss et al. | 604/264 |
| 4,968,307 | 2/1991 | Dake et al. | 604/264 |
| 4,995,865 | 2/1991 | Gahara et al. | 604/43 |
| 5,021,044 | 6/1991 | Sharkawy | 604/53 |

OTHER PUBLICATIONS

S. Mehta et al., "Rational Approach to Intracoronary Thrombolyis," *J. Invasive Cardiology* 4[6] Jul./Aug. 1992, pp. 306–311.
S. L. Kaufman et al., "Urokinase Thrombolysis Using a Multiple Side Hole Multilumen Infusion Catheter," Cardiovasc Intervent Radiol (1991) 14:334–337.
"The Unique Delivery System", Brochure, Peripheral Systems Group, ACS Co., 1989 (3 pp.).
"A Multiple-Flow Catheter with Multiple Advantages," Brochure, Mallinckrodt, undated (1 p.).
"McNamara Coaxial Catheter Infusion Set", Brochure, Cook, undated (2 pp.).
"Pulse* Spray Pulsed Infusion System", Brochure, Angiodynamics, E–Z–EM, Inc. (Nov. 91) (3 pp.).
"Pulse* Spray Pulsed Infusion System", Brochure, Angiodynamics, E–Z–EM, Inc., undated (28 pp.).
Hicks et al., "Multilevel Infusion Catheter for Use with Thrombolytic Agents," *J. Vascular & Interventional Radiology* 2 [1] Feb. 1991, pp. 73–75.

*Primary Examiner*—Corrine Maglione
*Attorney, Agent, or Firm*—Frances P. Craig

[57] ABSTRACT

An infusion catheter including an elongated catheter body, and an infusion section at its distal end for delivery of therapeutic fluid to bodily passages. The infusion section includes an outer tube and an inner tube concentric with the outer tube, each tube having a multiplicity of ports therethrough. The inner tube delimits a central, fluid delivery lumen. The inner tube is uniformly spaced apart from the outer tube to provide an annular passageway, the radial depth of the passageway being sufficient to permit fluid flow therewithin. Each of the ports through the outer tube provides fluid communication between the annular passageway and the exterior of the catheter, while each of the ports through the inner tube provides fluid communication between the central lumen and the annular passageway. Thus, therapeutic fluid can flow from the central lumen through the annular passageway to the catheter exterior. The catheter provides a uniform average flow rate of therapeutic fluid along the length of the infusion section by (a) providing a higher ratio of inner tube ports to outer tube ports in the distal portion than in the proximal portion of the infusion section, and/or (b) positioning the inner tube ports and outer tube ports relative to one another so that the average fluid flow distance in the annular passageway between the inner tube ports and the outer tube ports is smaller in the distal portion than in the proximal portion of the infusion section.

10 Claims, 3 Drawing Sheets

INFUSION CATHETER WITH UNIFORM DISTRIBUTION OF FLUIDS

BACKGROUND OF THE INVENTION

The present invention relates to infusion catheters for delivery of therapeutic fluids to bodily passages, and particularly to infusion catheters exhibiting uniform distribution of such therapeutic fluids along a length of the catheter.

In certain medical conditions, it is advantageous to deliver a therapeutic agent directly to a target region to avoid medicating the entire body and to limit the amount of therapeutic agent required for effective treatment. One example of such a medical condition is an arterial thrombus, or clot, which can be treated effectively by localized application of such therapeutic fluids as those containing tissue plasminogen activator, urokinase, or streptokinase.

Infusion catheters have been developed which can deliver therapeutic fluids directly to affected bodily passages, for example a thrombotic region of an artery. One type of infusion catheter is a hollow tube, the distal end of which has been pierced through its side wall to form multiple openings, or ports, providing direct access to the exterior for fluid flowing through a common central lumen. The ports are disposed at several axial positions along the infusion section to provide distribution of the therapeutic fluid along a desired length of the bodily passage. However, fluids flowing through a tube flow more readily from ports offering the least flow resistance. The longer the flow path followed by the fluid in the central lumen, the higher the resistance and the higher the pressure drop ($\Delta P$) in the fluid. If the infusion section of this catheter is more than a few centimeters long, the fluid flowing from each port exhibits resistance and a $\Delta P$ proportional to the fluid flow distance along the length of the central lumen. Thus, the fluid flowing to the more distal ports experiences higher $\Delta P$ than that flowing to the more proximal ports, and the fluid distribution is not uniform.

In another type of infusion catheter, the wall of the infusion section includes several small axial lumens each with a single opening or port to provide direct access to the exterior of the catheter for fluid flowing through each small lumen. The ports are disposed at different axial lengths along the infusion section to provide distribution to the desired length of the bodily passage. This design offers some improvement in distribution, but the varying lengths of the fluid flow paths still result in non-uniform flow over the length of the infusion section. Also, in this design the number of fluid delivery ports is limited by the small circumference of the infusion section tube.

It would be desirable to have an infusion catheter having an infusion section in which the resistance, or $\Delta P$, experienced by the fluid flowing to all the ports is equalized or balanced to provide uniform distribution of fluid along a desired length of a bodily passage. The infusion catheter described herein was developed to address that need.

SUMMARY OF THE INVENTION

In one aspect, the invention is an infusion catheter including an elongated catheter body having a proximal end and a distal end and having an infusion section at its distal end for delivery of therapeutic fluid to bodily passages. The infusion section has a proximal portion and a distal portion and includes a first infusion catheter tube having a wall delimiting a first lumen, the first tube wall having a multiplicity of first ports therethrough. The infusion section also includes a second infusion catheter tube disposed within and concentric with the first lumen, the second tube having a wall delimiting a second lumen. The second tube wall is uniformly spaced apart from the first tube wall to provide an annular passageway within the first lumen, the radial depth of the annular passageway being sufficient to permit fluid flow therewithin. The second tube wall has a multiplicity of second ports therethrough. Each of the first ports provides fluid communication between the annular passageway and the exterior of the catheter, while each of the second ports provides fluid communication between the second lumen and the annular passageway, so that the therapeutic fluid can flow from the second lumen through the second ports into the annular passageway, flow within the annular passageway, and flow from the annular passageway through the first ports to the catheter exterior. The ratio of the number of the second ports to the number of the first ports and the position of the first ports and the second ports relative to one another are selected to provide a substantially uniform average flow rate of the therapeutic fluid flowing from each of the first ports to the catheter exterior along the length of the infusion section.

In a narrower aspect, the ratio of the number of second ports to the number of first ports is higher in the distal portion than in the proximal portion of the catheter infusion section. In another narrower aspect, the first ports and second ports are positioned relative to one another so that the average fluid flow distance in the annular passageway between the second and first ports is smaller in the distal portion than in the proximal portion of the catheter infusion section.

In yet another narrower aspect, the catheter infusion section further includes at least one additional portion between the proximal portion and the distal portion, and the first ports and the second ports are positioned relative to one another so that the average fluid flow distance between the second ports and the first ports progressively decreases in the distal direction along the length of the infusion section.

BRIEF DESCRIPTION OF THE DRAWINGS

For a better understanding of the present invention, together with other objects, advantages, and capabilities thereof, reference is made to the following Description and appended claims, together with the Drawings in which:

DETAILED DESCRIPTION OF THE PREFERRED EMBODIMENTS

Figure 1:
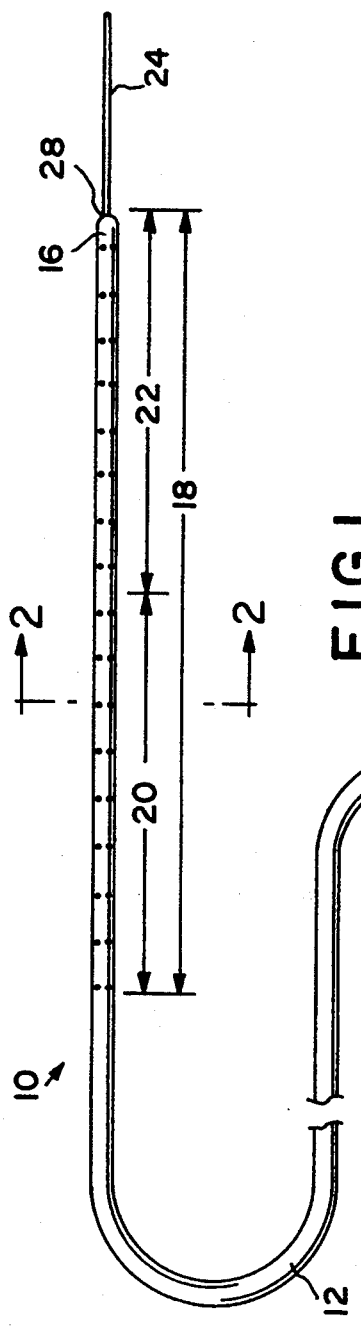
FIG. 1 is an elevation view of an infusion catheter in accordance with one embodiment of the present invention.

An exemplary embodiment of the infusion catheter in accordance with the invention has an infusion section formed from two cylindrical hollow tubes. A smaller tube is inserted concentrically into the lumen of a larger tube with an annular space between the tube walls. Openings, holes, or ports are provided in each tube for therapeutic fluid to flow from the interior of each tube to its exterior. The radial depth of the annular space is sufficient to permit the fluid to flow between the tubes from the inner tube ports to the outer tube ports. Thus therapeutic fluid supplied to the lumen of the inner tube can flow into the annular space between the tubes through the ports in the inner tube, and from the annular space to the exterior of the catheter through the ports in the outer tube.

In such a catheter, the fluid flow rate at any position along the length of the infusion section is proportional to $\Delta P$ (described above). The $\Delta P$, in turn, is affected not only by (a) the distance traveled by the fluid through the central lumen of the inner tube, but also by (b) the fluid flow volume supplied to the annular space and (c) the fluid flow distance through the annular space. Where the size of the inner and outer ports is uniform, as is convenient for ease of manufacture, the fluid flow volume through the annular space is greatly affected by the number of inner ports available for fluid flow relative to the number of outer ports. Further, the fluid flow distance through the annular space is influenced by the distance between adjacent inner and outer ports. Thus, the flow rate from ports at different axial positions along the infusion section can be regulated by the relative number and positions of the ports in the inner and outer tubes at that position.

The catheter described herein balances the fluid flow rate (a) by providing a smaller ratio of inner ports to outer ports in the proximal portion than in the distal portion, and/or (b) by providing a shorter average flow distance between the more distal inner and outer ports than between the more proximal inner and outer ports. Fluid traveling a longer distance within the central lumen of the catheter to reach the inner tube ports at the distal portion of the infusion section experiences a higher $\Delta P$ and slower fluid flow in the central lumen. The slower fluid flow can be compensated for by providing a higher ratio of inner ports to outer ports in the distal portion to increase the fluid volume supplied to the annular space. Alternatively or concurrently, the higher $\Delta P$ in the distal portion central lumen can be compensated for by allowing the fluid to travel a shorter average distance in the distal portion annular space than in that of the proximal portion, and experience a lower $\Delta P$ in the annular space before exiting the catheter. This may be accomplished by shortening the average fluid flow distance between adjacent inner and outer ports. Thus the fluid flow rate from different regions of the infusion section can be more uniform than in prior art catheters.

The description below of various illustrative embodiments shown in the Drawings is not intended to limit the scope of the present invention, but merely to be illustrative and representative thereof.

Referring now to FIG. 1, infusion catheter 10 includes elongated catheter body 12 having proximal end 14 and distal end 16. Infusion section 18 is provided at distal end 16 for delivery of therapeutic fluids to a thrombotic region of an artery (not shown). Infusion section 18 includes proximal portion 20 and distal portion 22. Guidewire 24 is threaded axially through catheter body 12 and infusion section 18, and is of sufficient length to extend proximally beyond fitting 26 and distally beyond distal tip 28 of distal end 16. Fitting 26 includes fluid inlet 30 for delivery of therapeutic fluid from, e.g., a syringe (not shown) to the catheter.

Figure 2:
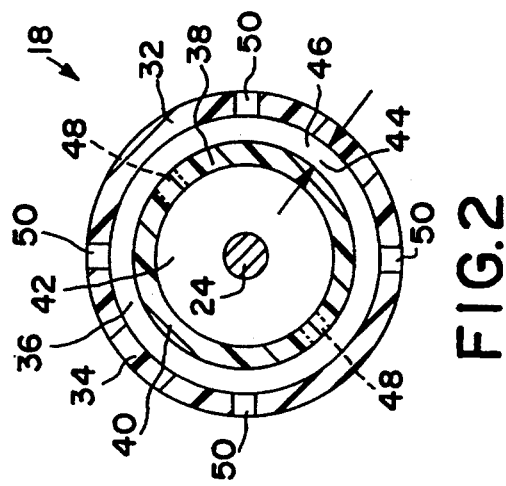
FIG. 2 is a radial cross-sectional view of the infusion section of the catheter of FIG. 1, taken along the line 2—2.

FIG. 2 is a radial cross-section of infusion section 18 of catheter 10, taken along line 2—2 of FIG. 1. Infusion section 18 includes outer tube 32 having tube wall 34 enclosing lumen 36. Infusion section 18 also includes inner tube 38 disposed within lumen 36 to be concentric with tube 32. Inner tube 38 has wall 40 enclosing central lumen 42 through which guidewire 24 passes. Tubes 32 and 38 are spaced apart by uniform radial distance 44 to form annular space or passageway 46 extending longitudinally between tube 32 and tube 38.

Tube 32 has four longitudinal rows of ports 50 perforating wall 34. Tube 38 has two longitudinal rows of ports 48 perforating wall 40. In the embodiment shown in FIG. 2, each of the rows of ports 48 is disposed between two of the rows of ports 50. However, in other embodiments the rows of ports may be otherwise disposed. Also, the number of rows of ports present in the inner and outer tubes may be different from one another, as shown, or may be the same. Alternatively, each row of inner ports may be aligned with a row of outer ports. As may be seen in FIG. 2, fluid communication exists between central lumen 42, annular passageway 46, and the exterior of infusion section 18 via ports 50 and 48.

Figure 3:
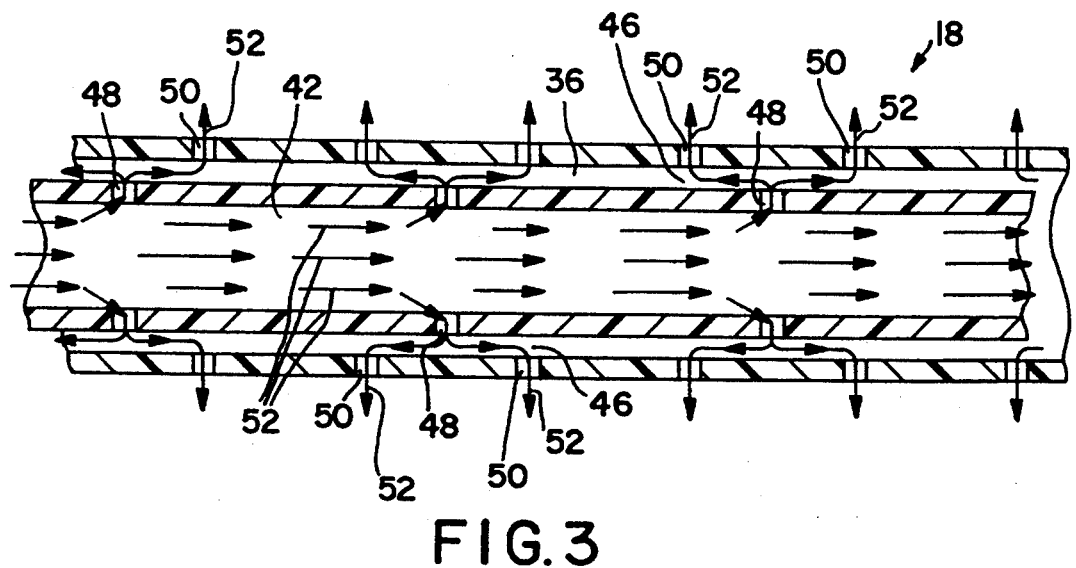
FIG. 3 is a schematic representation in longitudinal cross-section of a proximal portion of the infusion section of the catheter of FIGS. 1 and 2.
Figure 4:
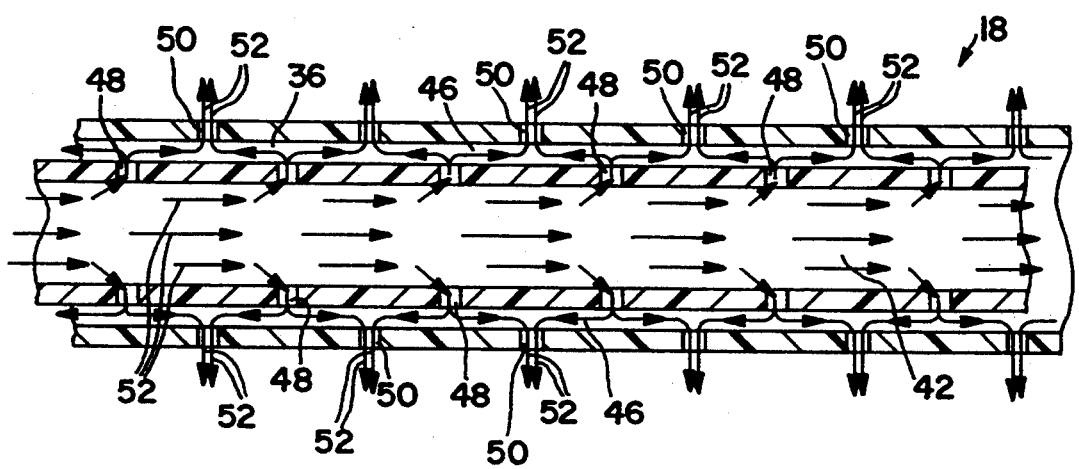
FIG. 4 is a schematic representation in longitudinal cross-section of a distal portion of the infusion section of the catheter of FIGS. 1 and 2.

FIGS. 3 and 4 schematically illustrate longitudinal cross-sections of portions of infusion section 18, showing the relative disposition of ports 48 and 50 in the proximal and distal portions, respectively, of infusion section 18. (For purposes of illustration, ports 48 are shown rotated 45° about the axis, not shown, of infusion section 18.) Arrows 52 in FIGS. 3 and 4 schematically illustrate the direction of flow of the therapeutic fluid within central lumen 42, through ports 48 into passageway 46, along passageway 46, and through ports 50 to the exterior of the catheter. For clarity, guidewire 24 is not shown in FIGS. 3 and 4.

As may be seen by a comparison of FIGS. 3 and 4, the number and spacing of outer tube ports 50 is the same in the proximal portion 20 and distal portion 22 of infusion section 18. However, the number of inner tube ports 48 in distal portion 22 is twice that in proximal portion 20, and the longitudinal spacing between inner tube ports 48 is reduced by half. This results in a greater volume of fluid flowing to each outer port 50 in distal portion 22 than in proximal portion 20. Also, arrows 52 show that, although the spacing between inner ports 48 is less, the average longitudinal distance traveled between adjacent inner and outer ports remains about the same. Thus in infusion catheter 10 of FIGS. 1–4, it is largely the difference in the ratios of the number of inner ports 48 to the number of outer ports 50 in the proximal and distal portions which balances the average flow rate of therapeutic fluid flowing to the catheter exterior along the length of infusion section 18.

Figure 5:
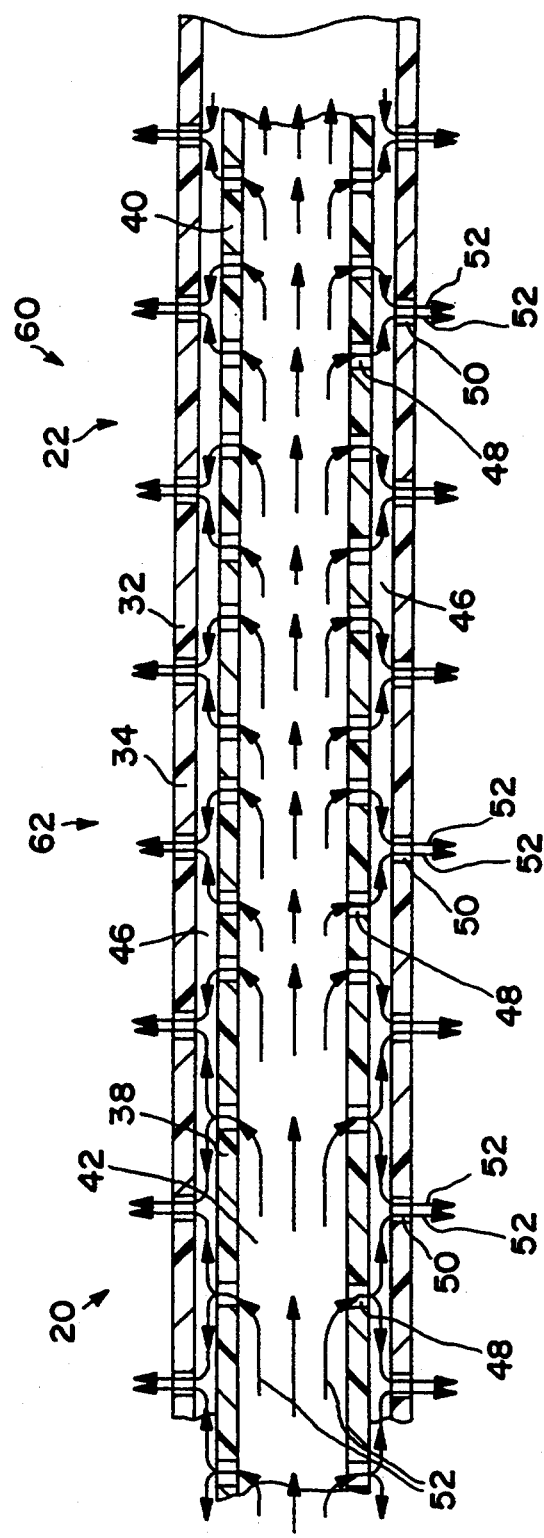
FIG. 5 is a schematic representation in longitudinal cross-section of the infusion section of an infusion catheter in accordance with an alternate embodiment of the invention.

FIG. 5 schematically represents a longitudinal cross-section of a portion of infusion section 60 in accordance with another embodiment of the invention. In FIG. 5, like features to those shown in FIGS. 1–4 are indicated by the same reference numerals. FIG. 5 shows the relative disposition of ports 48 and 50 in proximal portion 20, middle portion 62, and distal portion 22 of infusion section 18. (For purposes of illustration, ports 48 are shown rotated 45° about the axis, not shown, of infusion section 60 in a similar manner to the illustration of infusion section 18 of FIGS. 3 and 4.) As in FIGS. 3 and 4, arrows 52 schematically illustrate the direction of flow of the therapeutic fluid within central lumen 42, through ports 48 into passageway 46, along annular passageway 46, and through ports 50 to the exterior of the catheter. Also as in FIGS. 3 and 4, guidewire 24 is not shown.

In infusion section 60, outer tube 32 has four longitudinal rows of ports 50 perforating wall 34. Inner tube 38 has two longitudinal rows of ports 48 perforating wall 40. In the embodiment shown in FIG. 5, each of the rows of ports 48 is disposed between two of the rows of ports 50, similarly to the arrangement shown for infusion section 18 in FIG. 2. (As mentioned above, ports 48 are shown rotated 45° about the axis of infusion section 60.) However, in other embodiments the rows of ports may be otherwise disposed. Also, the number of rows of ports present in the inner and outer tubes may be different from one another, as shown, or may be the same. Alternatively, each row of inner ports may be aligned with a row of outer ports.

The number and spacing of outer tube ports 50 is the same in the proximal portion 20, middle portion 62, and distal portion 22 of infusion section 18. However, the number of inner tube ports 48 in middle portion 62 is greater than that in proximal portion 20, and the longitudinal spacing between inner tube ports 48 is reduced. This results in a greater volume of fluid flowing to each outer port 50 in middle portion 62 than in proximal portion 20. Also, unlike the catheter of FIGS. 1-4, arrows 52 in FIG. 5 show that the average longitudinal distance traveled between adjacent inner and outer ports is less in middle portion 62 than in proximal portion 20, and still less in distal portion 22. The number of inner tube ports 48 in distal portion 22, however, is the same as that in middle portion 62.

Thus in infusion catheter 60 of FIG. 5, two flow balancing mechanisms are in effect. Both of these mechanisms depend on providing concentric tubes 32 and 38 in infusion section 60 and on the relative placement of ports 48 and 50 in these tubes. The first flow balancing mechanism is the same as that described for infusion section 18 of FIGS. 1-4. That is, the difference in the ratios of the number of inner ports 48 to the number of outer ports 50 in the proximal and middle portions of infusion section 60 tends to balance the average volume of therapeutic fluid flowing to the catheter exterior from proximal portion 20 and middle portion 62.

The second flow balancing mechanism involves the average longitudinal distance travelled by the therapeutic fluid in annular passageway 46 and the effect this distance has on the $\Delta P$. As described above, the average longitudinal fluid flow distance decreases in the distal direction along the length of infusion section 62. Thus, in this mechanism, the progressively lower $\Delta P$ in passageway 46 from proximal portion 20 to distal portion 22 of infusion section 60 tends to offset the progressively higher $\Delta P$ along the length of central lumen 42. In short, in infusion section 60 both mechanisms are acting to provide a more uniform fluid flow between proximal portion 20 and middle portion 62, but the fluid flow between middle portion 62 and distal portion 22 is balanced principally by only a single mechanism.

In the embodiments shown in FIGS. 1-5, the spacing of outer tube ports 50 is uniform along the length of the infusion section while that of inner tube ports 48 varies to produce the flow balancing effects described above. In other embodiments, however, the outer tube port spacing may vary and the inner tube port spacing be uniform. Alternatively, the spacing of both the outer and inner tube ports may be varied along the length of the infusion section. Similarly, in the infusion sections illustrated, the ports are round and uniform in diameter along each tube and between the two tubes. Alternative embodiments, however, may have square, oval, rectangular, or other shaped ports, and their size need not be uniform along the length of each tube or uniform for the two tubes.

The infusion section of the catheters described above may be assembled using known techniques. Typically, the catheter body includes two concentric tubes, an outer catheter body tube providing the outer tube and being unitary therewith, and an inner catheter body tube providing the inner tube and being unitary therewith. Alternatively, a single, unitary tube may provide both a single-tube catheter body and either the outer tube or the inner tube of the infusion section, the other infusion section tube being bonded thereto by known means. Also alternatively, the inner and outer tubes may each be bonded to a separate catheter body tube. The central, fluid delivery lumen of the catheter body is in fluid communication with the central lumen of the inner tube (but not with the annular passageway). The tubing of the body and the infusion section may be fabricated from a polymer, e.g., a polyamide, or other flexible material conventional for infusion catheters, using an extruder or other conventional means. Both the inner and outer tubes of the infusion section are perforated to form the above-described ports, using such conventional means as a drill or laser. A conventional inlet fitting may be provided in the proximal end of the catheter body for delivery of therapeutic fluid to the catheter from, e.g., a syringe.

Typically, in operation a conventional guidewire, as 24, is manipulated, using known techniques, through the bodily passages of a patient to reach the region needing treatment. The infusion catheter described above, including the novel infusion section, as 18 or 60, is then threaded onto the guidewire and manipulated into position with the infusion section adjacent the region needing treatment. A syringe or other known fluid medication providing device is used to provide therapeutic fluid under pressure to inlet 30, catheter body 12, and central lumen 42 of the infusion section. The fluid flows through central lumen 42, through inner tube ports 48, through annular passageway 46, and through outer tube ports 50, as described above, to deliver the therapeutic fluid to the treated region of the bodily passage. One or both of the fluid balancing mechanisms described above operates to provide a more uniform distribution of therapeutic fluid along the length of the infusion section than has been possible with prior art infusion catheters.

The invention described herein presents to the art novel, improved infusion catheters having the advantage of more uniform application of therapeutic fluids along the length of the infusion section. The improved fluid flow from the distal end of the infusion section can also enable the use of longer length infusion sections without the problems of non-uniform flow associated with prior art infusion catheters.

While there has been shown and described what are at present considered the preferred embodiments of the invention, it will be apparent to those skilled in the art that modifications and changes can be made therein without departing from the scope of the present invention as defined by the appended claims.

We claim:

1. An infusion catheter comprising an elongated catheter body having a proximal end and a distal end and having an infusion section at its distal end for delivery of therapeutic fluid to bodily passages, said infusion section having a proximal portion and a distal portion and comprising:

a first infusion catheter tube having a wall delimiting a first lumen, said first tube wall having a multiplicity of first ports therethrough; and a second infusion catheter tube disposed within and concentric with said first lumen, said second tube having a wall delimiting a second lumen, said second tube wall being uniformly spaced apart from said first tube wall to provide an annular passageway within said first lumen, the radial depth of said annular passageway being sufficient to permit fluid flow therewithin, said second tube wall having a multiplicity of second ports therethrough;

wherein each of said first ports provides fluid communication between said annular passageway and the exterior of said catheter and each of said second ports provides fluid communication between said second lumen and said annular passageway such that said therapeutic fluid can flow from said second lumen through said second ports into said annular passageway, flow within said annular passageway, and flow from said annular passageway through said first ports to said catheter exterior; and the said first ports and said second ports are positioned relative to one another such that the average fluid flow distance in said annular passageway between said second ports and said first ports is smaller in said infusion section distal portion than in said infusion section proximal portion to provide a substantially uniform average flow rate of said therapeutic fluid flowing from each of said first ports to said catheter exterior along the length of said infusion section.

2. An infusion catheter in accordance with claim 1 wherein said first ports are disposed equidistant from one another in the axial direction and equidistant from one another in the circumferential direction to form a regular array of first ports in said first tube wall; and said second ports are disposed equidistant from one another in the circumferential direction but are disposed axially at distances from one another selected such that said average fluid flow distance between said second ports and said first ports is smaller in said distal portion than in said proximal portion.

3. An infusion catheter in accordance with claim 1 wherein said infusion section further comprises at least one additional portion between said proximal portion and said distal portion, and wherein said first ports and said second ports are positioned relative to one another such that the average fluid flow distance between said second ports and said first ports progressively decreases in the distal direction along the length of said infusion section.

4. An infusion catheter in accordance with claim 3 wherein said first ports are disposed equidistant from one another in the axial direction and equidistant from one another in the circumferential direction to form a regular array of first ports in said first tube wall; and said second ports are disposed equidistant from one another in the circumferential direction but are disposed axially at distances from one another selected such that said average fluid flow distance between said second ports and said first ports progressively decreases in the distal direction along the length of said infusion section.

5. An infusion catheter in accordance with claim 1 wherein said catheter body comprises a catheter body tube from which said infusion section extends, said catheter body tube having a fluid delivery lumen in fluid communication with said second lumen, said infusion catheter further comprising inlet means in said catheter body proximal end for delivery of said therapeutic fluid from a therapeutic fluid source to said fluid delivery lumen.

6. An infusion catheter in accordance with claim 5 wherein said catheter body tube comprises outer and inner catheter body tubes, said outer tube being unitary with said first tube and said inner tube being unitary with said second tube, said inner tube providing said fluid delivery lumen in fluid communication with said second lumen.

7. An infusion catheter comprising an elongated catheter body having a proximal end and a distal end and having an infusion section at its distal end for delivery of therapeutic fluid to bodily passages, said infusion section having a proximal portion and a distal portion and comprising:

a first infusion catheter tube having a wall delimiting a first lumen, said first tube wall having a multiplicity of first ports therethrough; and a second infusion catheter tube disposed within and concentric with said first lumen, said second tube having a wall delimiting a second lumen, said second tube wall being uniformly spaced apart from said first tube wall to provide an annular passageway within said first lumen, the radial depth of said annular passageway being sufficient to permit fluid flow therewithin, said second tube wall having a multiplicity of second ports therethrough;

wherein each of said first ports provides fluid communication between said annular passageway and the exterior of said catheter and each of said second ports provides fluid communication between said second lumen and said annular passageway such that said therapeutic fluid can flow from said second lumen through said second ports into said annular passageway, flow within said annular passageway, and flow from said annular passageway through said first ports to said catheter exterior; and the ratio of the number of said second ports to the number of said first ports is higher in said infusion section distal portion than in said infusion section proximal portion to provide a substantially uniform average flow rate of said therapeutic fluid flowing from each of said first ports to said catheter exterior along the length of said infusion section.

8. A catheter in accordance with claim 7 wherein said first ports and said second ports are positioned relative to one another such that the average fluid flow distance in said annular passageway between said second ports and said first ports is smaller in said distal portion than in said proximal portion.

9. An infusion catheter in accordance with claim 7 wherein said catheter body comprises a catheter body tube from which said infusion section extends, said catheter body tube having a fluid delivery lumen in fluid communication with said second lumen, said infusion catheter further comprising inlet means in said catheter body proximal end for delivery of said therapeutic fluid from a therapeutic fluid source to said fluid delivery lumen.

10. An infusion catheter in accordance with claim 9 wherein said catheter body tube comprises outer and inner catheter body tubes, said outer tube being unitary with said first tube and said inner tube being unitary with said second tube, said inner tube providing said fluid delivery lumen in fluid communication with said second lumen.

* * * * *